(12) United States Patent
Nguyen et al.

(10) Patent No.: US 7,810,502 B1
(45) Date of Patent: Oct. 12, 2010

(54) ANTI-SNORING AND OBSTRUCTIVE SLEEP APNEA DEVICE

(76) Inventors: Nghiep V. Nguyen, 18056 Waco Dr. NW., Ramsey, MN (US) 55303-3395;
Corinee J. Nguyen, 18056 Waco Dr. NW., Ramsey, MN (US) 55303-3395

( * ) Notice: Subject to any disclaimer, the term of this patent is extended or adjusted under 35 U.S.C. 154(b) by 0 days.

(21) Appl. No.: 11/942,007

(22) Filed: Nov. 19, 2007

(51) Int. Cl.
*A61F 5/56* (2006.01)
*A61C 5/14* (2006.01)
*A61C 3/00* (2006.01)

(52) U.S. Cl. .................. 128/848; 128/859; 128/861; 433/6

(58) Field of Classification Search .............. 128/848, 128/859, 860, 861, 862; 433/18, 19, 22, 433/5, 6; 602/902; 600/240
See application file for complete search history.

(56) References Cited

U.S. PATENT DOCUMENTS

| | | | | |
|---|---|---|---|---|
| 4,708,646 A | * | 11/1987 | Jasper | 433/19 |
| 5,499,633 A | * | 3/1996 | Fenton | 128/848 |
| 6,074,207 A | * | 6/2000 | Coats | 433/19 |

* cited by examiner

*Primary Examiner*—Patricia M Bianco
*Assistant Examiner*—Ophelia Hawthorne
(74) *Attorney, Agent, or Firm*—David A. Lingbeck

(57) ABSTRACT

An anti-snoring and obstructive sleep apnea device for preventing one's lower jaw from receding and preventing one's tongue from blocking the air passageway thus eliminating one's snoring. The anti-snoring and obstructive sleep apnea device includes an first support being removably retained by a user's upper teeth; and also includes a second support being supported by a user's lower teeth; and further includes an assembly being retained to the first support for positioning the second support and preventing the lower jaw from receding and the tongue from blocking the air passageway of a user and to allow the user to open one's mouth and to move one's lower jaw forwardly and laterally.

17 Claims, 5 Drawing Sheets

ANTI-SNORING AND OBSTRUCTIVE SLEEP APNEA DEVICE

BACKGROUND OF THE INVENTION

1. Field of the Invention

The present invention relates to anti-snoring and obstructive sleep apnea devices and more particularly pertains to a new anti-snoring and obstructive sleep apnea device for preventing one's lower jaw from receding thus preventing the tongue from blocking the airway and eliminating one's snoring.

2. Description of the Prior Art

The use of anti-snoring and obstructive sleep apnea devices is known in the prior art. More specifically, anti-snoring and obstructive sleep apnea devices heretofore devised and utilized are known to consist basically of familiar, expected and obvious structural configurations, notwithstanding the myriad of designs encompassed by the crowded prior art which have been developed for the fulfillment of countless objectives and requirements.

The prior art includes bite blocks which are essentially mounted to the upper and lower arches with a connector which rigidly sets the position of the lower bite block relative to the upper bite block with the user being very limited with lateral movement.

SUMMARY OF THE INVENTION

The general purpose of the present invention, which will be described subsequently in greater detail, is to provide a new anti-snoring and obstructive sleep apnea device which has many of the advantages of the anti-snoring and obstructive sleep apnea devices mentioned heretofore and many novel features that result in a new anti-snoring and obstructive sleep apnea device which is not anticipated, rendered obvious, suggested, or even implied by any of the prior art anti-snoring and obstructive sleep apnea devices, either alone or in any combination thereof. The present invention includes a first support being removably retained by a user's upper teeth; and also includes a second support being supported by a user's lower teeth; and further includes an assembly being connected to the first support for positioning the second support and preventing the tongue from blocking the air passageway of a user and to allow the user to open one's mouth and to move one's lower jaw forwardly and laterally. None of the prior art includes the combination of the elements of the present invention.

There has thus been outlined, rather broadly, the more important features of the anti-snoring and obstructive sleep apnea device in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new anti-snoring and obstructive sleep apnea device which has many of the advantages of the anti-snoring and obstructive sleep apnea devices mentioned heretofore and many novel features that result in a new anti-snoring and obstructive sleep apnea device which is not anticipated, rendered obvious, suggested, or even implied by any of the prior art anti-snoring and obstructive sleep apnea devices, either alone or in any combination thereof.

Still another object of the present invention is to provide a new anti-snoring and obstructive sleep apnea device for preventing one's lower jaw from receding thus preventing the tongue from falling into the air passageway and thus eliminating one's snoring.

Still yet another object of the present invention is to provide a new anti-snoring and obstructive sleep apnea device that allows lateral and forward movement of one's lower jaw.

Even still another object of the present invention is to provide a new anti-snoring and obstructive sleep apnea device that allows the user to open one's mouth during the use thereof and also allows for precise adjustment of the device while the device is disposed in the user's mouth either by the user doing the adjusting or by a clinical staff member or someone else making the adjustment of the user's lower arch even while the user is asleep and until the snoring ceases.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
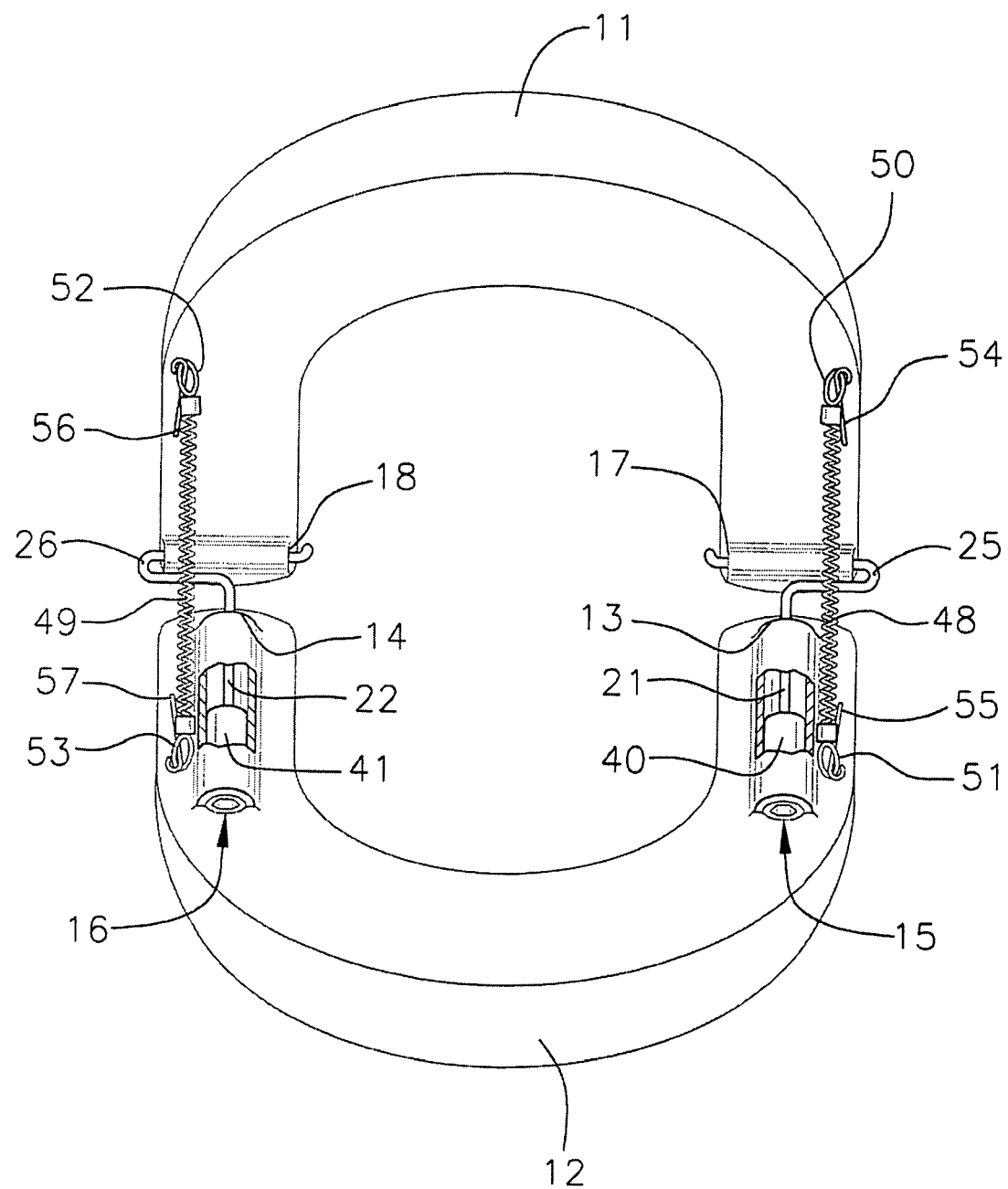
FIG. 1 is a front perspective view of a new anti-snoring and obstructive sleep apnea device according to the present invention.
Figure 2:
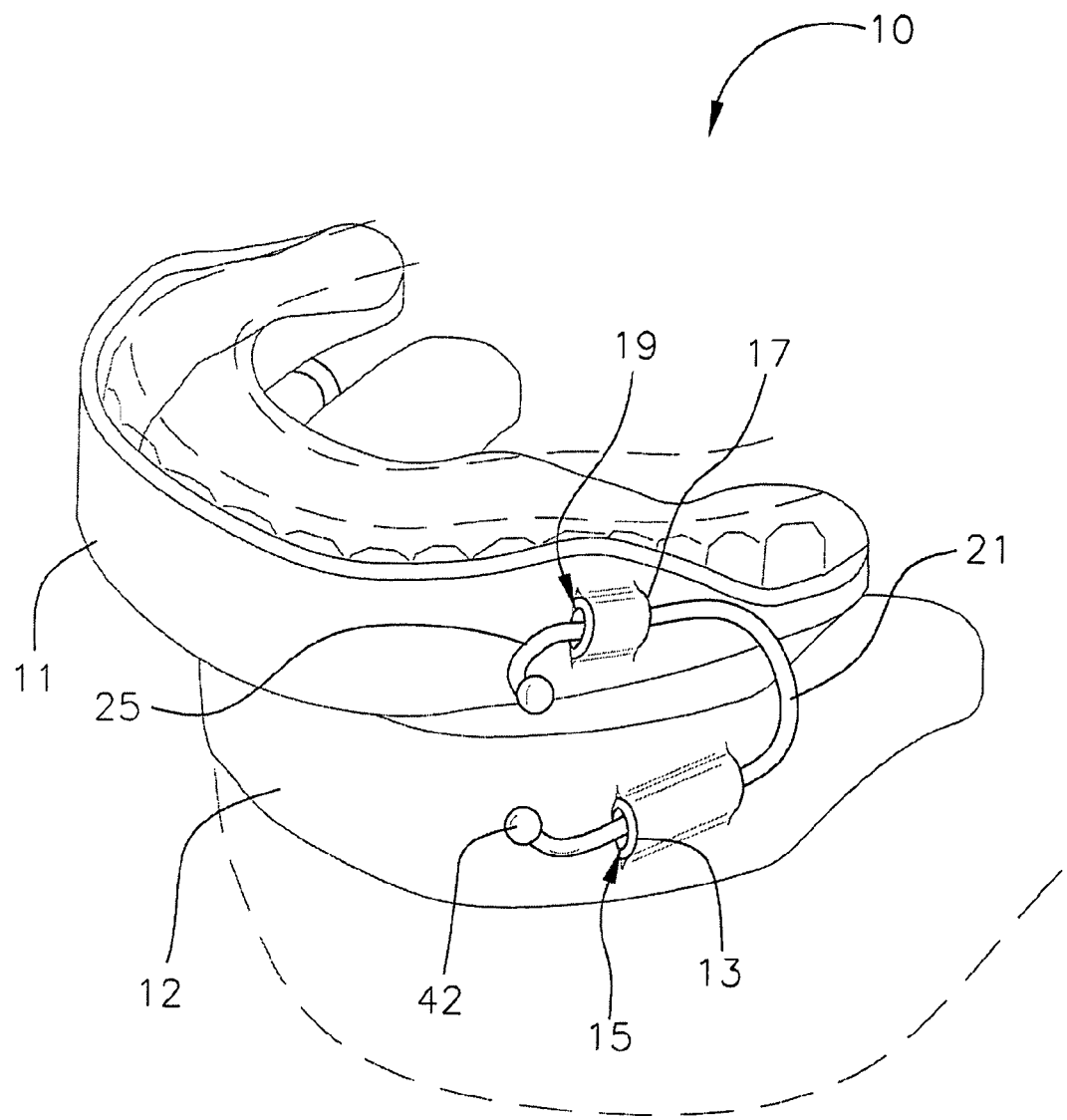
FIG. 2 is a front perspective view of a second embodiment of the present invention.
Figure 3:
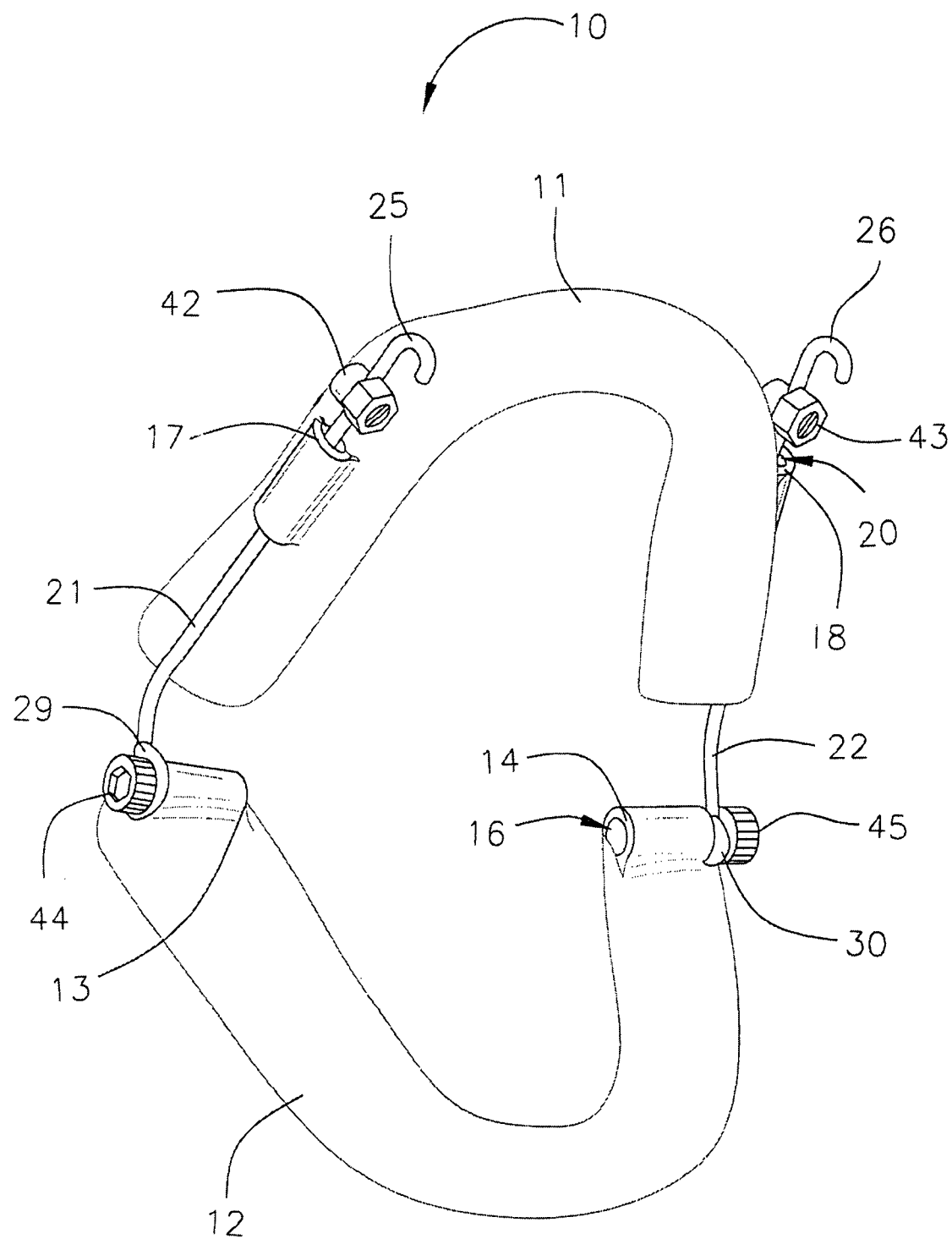
FIG. 3 is a front perspective view of a fifth embodiment of the present invention.
Figure 4:
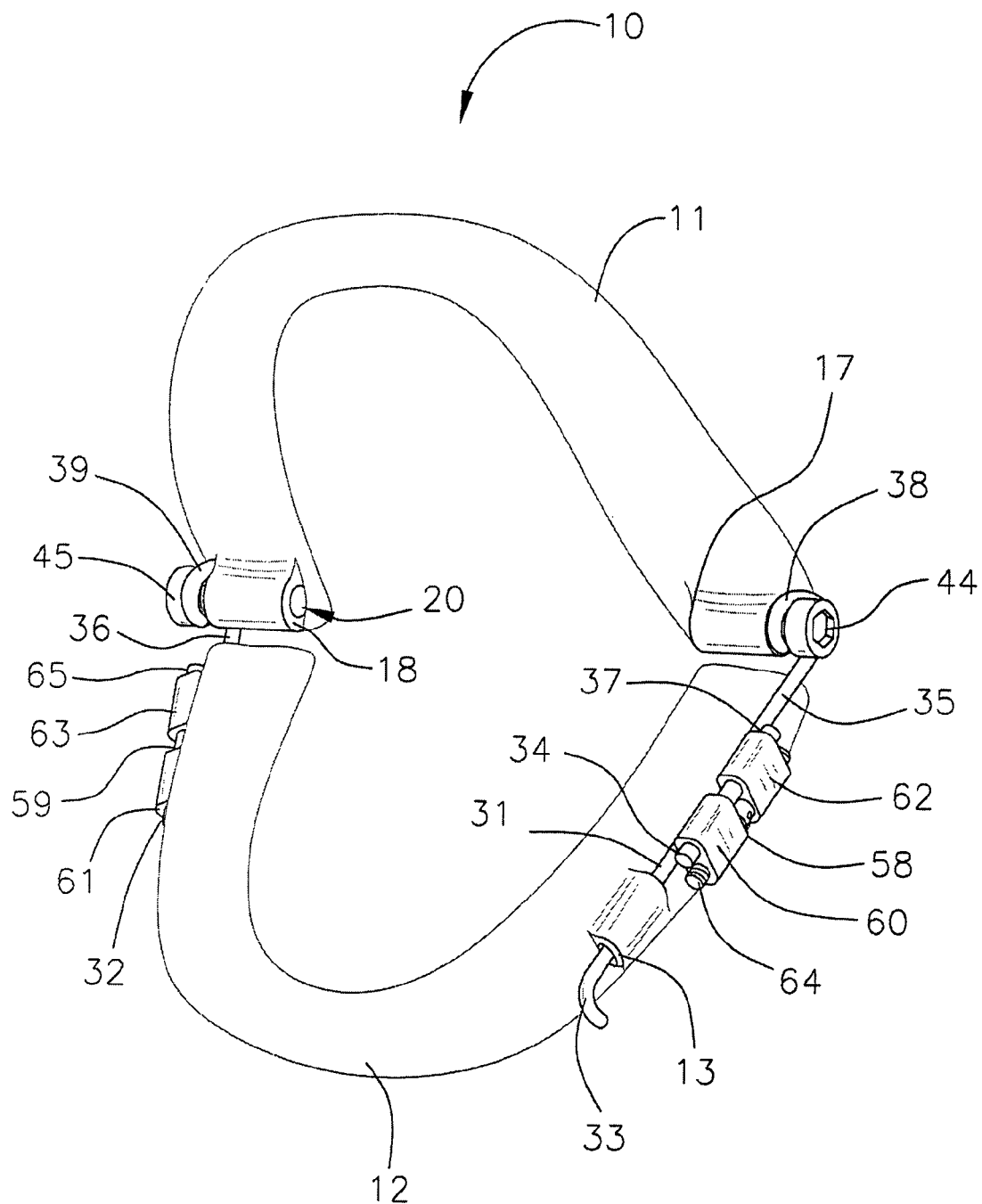
FIG. 4 is a front perspective view of a fourth embodiment of the present invention.
Figure 5:
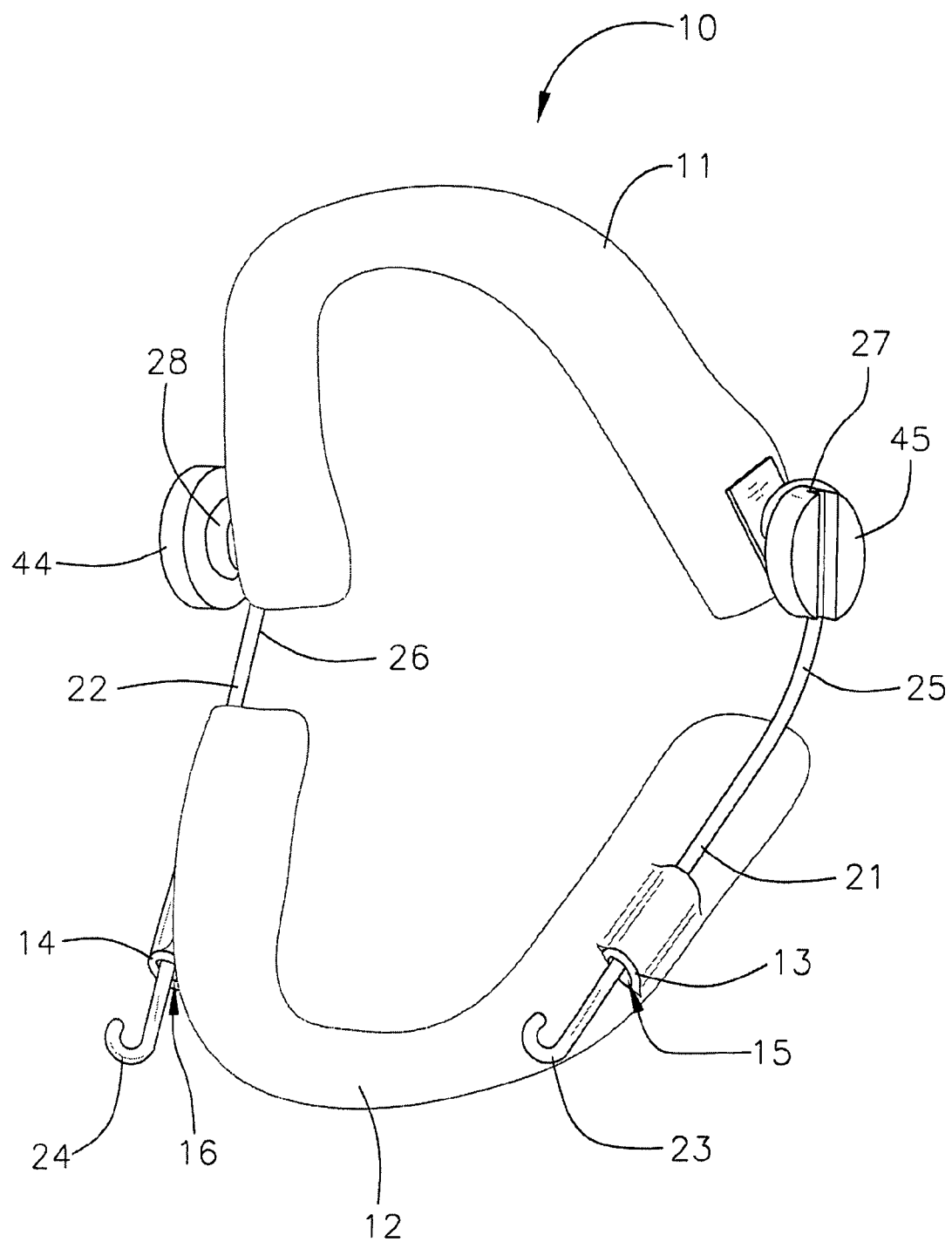
FIG. 5 is a front perspective view of the third embodiment of the present invention.

With reference now to the drawings, and in particular to FIGS. 1 through 5 thereof, a new anti-snoring and obstructive sleep apnea device embodying the principles and concepts of the present invention and generally designated by the reference numeral 10 will be described.

As best illustrated in FIGS. 1 through 5, the anti-snoring and obstructive sleep apnea device 10 generally comprises a first support 11 being removably and conventionally retained by a user's upper teeth, and also comprises a second support 12 being conventionally supported by a user's lower teeth, and further comprises an assembly being retained to the first support 11 for positioning the second support 12 and preventing the tongue from blocking the air passageway of a user and to allow the user to move one's lower jaw relative to the upper jaw especially laterally. The assembly includes elongate tubular members 13,14 being securely imbedded in the second support 12 and each having a bore 15,16 being disposed therethrough. The elongate tubular members 13,14 are securely and conventionally embedded buccally near the distal of the second support 12 and are arranged such that the longitudinal axis of each elongate tubular member 13,14 is parallel to a longitudinal axis of a respective end portion of the second support 12. The assembly further includes support members 17,18 being conventionally embedded into the first support 11. The assembly also includes guide members 21,22 being supported by the first support 11 and being in communication to the elongate tubular members 13,14.

In a first embodiment, the support members 17,18 include tubular support members 17,18 each having a bore 19,20 being disposed therethrough with the tubular support members 17,18 being conventionally attached near the distal of the first support 11. The guide members 21,22 are wires each having a first end portion 23,24 being movably disposed in the bore 15,16 of the respective elongate tubular member 13,14. The assembly further includes stoppers 40,41 each being adjustably threaded in an end of the bore 15,16 of the respective elongate tubular member 13,14 and being in contactable relationship to the respective wire 21,22 to forwardly position the second support 12 relative to the first support 11 so that the user's lower jaw is not blocking the user's air passageway. The wires 21,22 each have a second end portion 25,26 which has a sideways-oriented U-shape to allow the second end portion 25,26 of the wire 21,22 to extend through the bore 19,20 of the respective tubular support member 17,18 so that the tubular support member 17,18 can pivot about the second end portion 25,26 of the wire 21,22.

In a second embodiment, each of the first end portions 23,24 of the wires 21,22 is disposed through the bore 15,16 of the respective elongate tubular member 13,14. The assembly includes stop members 42,43 each being conventionally attached near an end of the first end portion 23,24 of the respective wire 21,22 to prevent the wire 21,22 from coming out of the respective elongate tubular member 13,14. The wires 21,22 each have a second end portion 25,26 which is disposed through the bore 19,20 of the respective tubular support member 17,18 with the second end portion 25,26 having a curved end to prevent the respective wire 21,22 from coming out of the bore 19,20 of the respective tubular support member 17,18.

In a third embodiment, the guide members 21,22 are wires each having a first end portion 23,24 which has a hooked shaped end to prevent the first end portion from coming out of respective elongate tubular member 13,14 and also having a second end portion 25,26 which is curved relative to the first end portion 23,24 and which has a hook-shaped end 27,28 which is pivotally supported upon a fastener 44,45 which is conventionally fastened to the first support 11 to allow the second support 12 to be moved relative to the first support 11 which allows the user to open and close one's mouth.

In a fourth embodiment, the hook-shaped end 27,28 is pivotally and conventionally supported upon a fastener 44,45 which is fastened in the bore 19,20 of the respective tubular support member 17,18.

In a fifth embodiment, the wires 21,22 each has a first end portion which has an eyelet 29,30 conventionally attached at an end thereof. The eyelet 29,30 is conventionally supported upon a respective fastener 44,45 which is fastened in the bore of a respective elongate tubular member 13,14 to allow the second support to be moved relative to the first support which allows the user to open and close one's mouth. Each wire 21,22 further has a second end portion 25,26 being movably disposed through the bore 19,20 of a respective tubular support member 17,18 and has a curved end to prevent the second end portion 25,26 from coming out of the respective tubular support member 17,18. The assembly further has stop members 42,43 being adjustably and conventionally attached to the wires 21,22 near the curved end of the second end portion 25,26.

The fourth embodiment further includes the guide members 21,22 having first wires 31,32 being movably disposed through the elongate tubular members 13,14 and with the first wires 31,32 having a curved first end 33 to prevent the first wires 31,32 from coming out of the elongate tubular members 14. The guide members 21,22 also include second wires 35,36 having a hook-shaped second end 38,39 which are conventionally supported upon fasteners 44,45 which are fastened in the bores 19,20 of the tubular support members 17,18. The assembly further includes adjustable connectors 58,59 being conventionally connected to second ends 34 of the first wires 31,32 and being connected to first ends 37 of the second wires 35,36. The adjustable connectors 58,59 include first connecting members 60,61 being conventionally connected to the first wires 31,32 and also include second connecting members 62,63 being conventionally connected to the second wires 35,36. The adjustable connectors 58,59 further include threaded fastening members 64,65 conventionally interconnecting the first and second connecting members 60-63.

For the first embodiment, the assembly also includes spring members 48,49 being removably and conventionally attached to the first support 11 and to the second support 12 to bias the first support 11 in close proximity to the second support 12. The spring members 48,49 have ring members 50-53 at ends thereof. The ring members 50-53 are removably supported upon hook members 54-57 which are securely and conventionally attached to the first support 11 and to the second support 12.

In addition, for the first and fourth embodiments, the tubular support members 17,18 are conventionally attached to end portions of the first support 11 and each has a longitudinal axis which is disposed generally perpendicular to a longitudinal axis of the respective end portion of the first support 11.

In use, the user, prior to going to sleep, places the anti-snoring and obstructive sleep apnea device 10 in one's mouth with the user putting one's upper teeth in the first support 11 and then putting the second support 12 about the user's lower teeth. The assembly is set either prior to or while the anti-snoring and obstructive sleep apnea device 10 is placed in one's mouth such that the second support 12 prevents the user's lower jaw from receding and preventing the user's tongue from falling into the air passageway which causes the person to snore. The assembly moves the user's lower jaw forwardly to keep the air passageway free of obstruction from the user's tongue.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the anti-snoring and obstructive sleep apnea device. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. An anti-snoring and obstructive sleep apnea device comprising:
a first support being removably retained by a user's upper teeth;
a second support being supported by a user's lower teeth; and
an assembly being retained to said first support for positioning said second support and preventing the lower jaw from receding and preventing a user's tongue from being in the air passageway of a user and to allow the user to move one's mouth and to move one's lower jaw relative to the user's upper jaw, said assembly including at least one elongate tubular member being securely embedded in said second support and having a bore disposed therethrough, said assembly further including at least one support member being embedded in said first support.

2. The anti-snoring and obstructive sleep apnea device as described in claim 1, wherein said assembly also includes at least one guide member being supported by said first support and being in communication to said at least one elongate tubular member.

3. The anti-snoring and obstructive sleep apnea device as described in claim 2, wherein said at least one support member includes at least one tubular support member having a bore disposed therethrough with said at least one tubular support member being embedded to the distal of said first support.

4. The anti-snoring and obstructive sleep apnea device as described in claim 3, wherein said at least one guide member includes at least one wire having a first end portion being movably disposed in said bore of said at least one elongate tubular member.

5. The anti-snoring and obstructive sleep apnea device as described in claim 4, wherein said assembly further includes at least one stopper being adjustably threaded in an end of said bore of said at least one elongate tubular member and being in contactable relationship to said at least one wire, said at least one stopper adjustably positioning said second support relative to said first support to prevent the user's lower jaw from receding and the user's tongue from blocking the user's air passageway.

6. The anti-snoring and obstructive sleep apnea device as described in claim 5, wherein said at least one wire has a second end portion which has a sideways-oriented U-shape to allow said second end portion of said at least one wire to extend through said bore of said at least one tubular support member, so that said at least one tubular support member can pivot about said second end portion of said at least one wire.

7. The anti-snoring and obstructive sleep apnea device as described in claim 3, wherein said at least one guide member includes at least one first wire being movably disposed through said at least one elongate tubular member and having a curved first end to prevent said at least one first wire from coming out of said at least one elongate tubular member, said at least one guide member also including at least one second wire having a hook-shaped second end which is supported upon a fastener which is fastened in said bore of said at least one tubular support member.

8. The anti-snoring and obstructive sleep apnea device as described in claim 7, wherein said assembly further includes at least one adjustable connector being connected to a second end of said at least one first wire and being connected to a first end of said at least one second wire, said at least one adjustable connector including a first connecting member being connected to said at least one first wire and also including a second connecting member being connected to said at least one second wire, said at least one adjustable connector further including at least one threaded fastening member interconnecting said first and second connecting members.

9. The anti-snoring and obstructive sleep apnea device as described in claim 3, wherein said at least one wire has a first end portion which has an eyelet at an end thereof, said eyelet being supported upon at least one fastener which is fastened in said bore of said at least one elongate tubular member to allow said second support to be moved relative to said first support which allows the user to open and close one's mouth, said at least one wire further having a second end portion being movably disposed through said bore of said at least one tubular support member and having a curved end to prevent said second end portion from coming out of said at least one tubular support member, said assembly further having at least one stop member being adjustably attached to said at least one wire near said curved end of said second end portion.

10. The anti-snoring and obstructive sleep apnea device as described in claim 3, wherein said at least one tubular support member is attached to an end portion of said first support and has a longitudinal axis which is disposed generally perpendicular to a longitudinal axis of said end portion of said first support and to a longitudinal axis of said at least one elongate tubular member.

11. The anti-snoring and obstructive sleep apnea device as described in claim 4, wherein said first end portion of said at least one wire is disposed through said bore of said at least one elongate tubular member.

12. The anti-snoring and obstructive sleep apnea device as described in claim 11, wherein, said assembly includes a stop member being attached near an end of said first end portion of said at least one wire to prevent said at least one wire from coming out of said at least one elongate tubular member.

13. The anti-snoring and obstructive sleep apnea device as described in claim 12, wherein said at least one wire has a second end portion which is disposed through said bore of said at least one tubular support member, said second end portion having a curved end to prevent said at least one wire from coming out of said bore of said at least one tubular support member.

14. The anti-snoring and obstructive sleep apnea device as described in claim 6, wherein said at least one guide member includes at least one wire having a first portion which is movably disposed through said bore of said at least one elongate tubular member and which has a curved end to prevent said first portion from coming out of said at least one elongate tubular member, and also having a second end portion which has a hook-shaped end which is pivotally supported upon at least one fastener which is fastened to said first support to allow said second support to be moved relative to said first support which allows the user to open and close one's mouth.

15. The anti-snoring and obstructive sleep apnea device as described in claim 14, wherein said hook-shaped end is pivotally supported upon at least one fastener which is fastened in said bore of said at least one tubular support member.

16. The anti-snoring and obstructive sleep apnea device as described in claim 2, wherein said assembly also includes at least one spring member being removably attached to said first support and to said second support to bias said first support in close proximity to said second support.

17. The anti-snoring and obstructive sleep apnea device as described in claim 16, wherein said at least one spring member has ring members at ends thereof, said ring members being removably supported upon hook members which are securely attached to said first support and to said second support.

\* \* \* \* \*

UNITED STATES PATENT AND TRADEMARK OFFICE
CERTIFICATE OF CORRECTION

PATENT NO.        : 7,810,502 B1                                    Page 1 of 1
APPLICATION NO.   : 11/942007
DATED             : October 12, 2010
INVENTOR(S)       : Nghiep V. Nguyen and Corinne J. Nguyen It is certified that error appears in the above-identified patent and that said Letters Patent is hereby corrected as shown below:

On the Title page, Item (76) Should not be spelled "Corinee". Correct spelling is "Corinne".

Signed and Sealed this

Seventh Day of December, 2010

David J. Kappos
*Director of the United States Patent and Trademark Office*